United States Patent [19]

Pieczenik

[11] Patent Number: 5,560,379
[45] Date of Patent: Oct. 1, 1996

[54] DENTAL PAPER PICK AND FLOSSER

[76] Inventor: George Pieczenik, 61 W. 62nd St. Apt. 11G, New York, N.Y. 10023

[21] Appl. No.: 289,631

[22] Filed: Aug. 12, 1994

[51] Int. Cl.$^6$ ................................................. A61C 15/00
[52] U.S. Cl. ............................................................ 132/329
[58] Field of Search ................................ 132/321, 329

[56] References Cited

U.S. PATENT DOCUMENTS

| 725,081 | 4/1903 | Hills | 132/329 |
|---|---|---|---|
| 1,462,062 | 7/1923 | Browning | 132/329 |
| 1,468,125 | 9/1923 | Nielsen | 132/329 |
| 1,927,455 | 9/1933 | John | 132/329 |
| 2,035,425 | 3/1936 | Doll | 132/329 X |
| 2,760,628 | 8/1956 | Briggs | 132/329 X |
| 2,925,087 | 2/1960 | Kucher | 132/329 |
| 3,247,857 | 4/1966 | Kanbar | 132/329 |
| 4,237,911 | 12/1980 | White | 132/329 |
| 4,312,370 | 1/1982 | Hinge | 132/329 |
| 5,293,886 | 3/1994 | Czapor | 132/329 |

FOREIGN PATENT DOCUMENTS

| 1255629 | 1/1961 | France | 132/329 |
|---|---|---|---|
| 2059266 | 4/1981 | United Kingdom | 132/329 |

Primary Examiner—Nicholas D. Lucchesi

[57] ABSTRACT

A conveniently portable dental cleaning instrument and kit for cleaning the interproximal area between teeth and crevices within and between teeth and gums are described. It can be constructed from siliconized paper, treated paper, cellophanes, and thin plastics. The preferred embodiment is a specific, double-sided siliconized paper, which has been determined to be of sufficient tensile strength, sturdiness, smoothness, having a low frictional coefficient, and flexible enough to be foldable without cracking. This embodiment allows the user to remove particles and plaque build-up in the interproximal spaces and dental crevices by using normal flossing and tooth-picking type strokes. Unlike flossing threads and wooden toothpicks, this invention will not dislodge fillings or remove loose caps, temporary caps, or bridge-work.

This dental paper and kit can, also, be prepared with embedded microspheres containing flavors, sweeteners, dentifrices and antiseptics for additional hygienic, social, and anti-smoking uses.

5 Claims, 2 Drawing Sheets

DENTAL PAPER PICK AND FLOSSER

BACKGROUND

1. Field of the Invention

This invention relates to an improved method of picking and flossing teeth by using a specially formulated siliconized paper that can be inserted between teeth and folded to allow flossing and picking of dental crevices. This invention further relates to a kit that allows the user to carry several such papers in a large matchbook type holder.

2. Description of Prior Art

This invention concerns dental floss and tooth picks and the use, therein, for preventive, corrective and maintaining dental and gum care. One particular type of dental floss, which is by far the most commonly used, is merely a multi-filament nylon thread formed as a long strand about a spool for easy dispensing.

For flossing with this nylon thread dentist and manufacturers recommend cutting an 18–30 inch segment and using a 2–3 inch segment somewhere along the length, and the thread is wound about the index fingers of both hands to floss. The exposed section is inserted into the space between adjacent teeth. Once in position, the section of nylon floss is moved forward and backward against the tooth surface, either length wise or in a transverse of the tooth.

A tooth pick normally made of wood (white birch, Richwood Toothpicks) or plastic is normally used to remove food particles and/or decay from within teeth and between teeth and between tooth and gum. Contemporary toothpicks are also advertised as being "plaque removers" and "fight gum disease" and are to be used moistened and in a gentle in- and -out motion between teeth. Johnson and Johnson's "STIMU-DENT" makes such claims.

The purpose of flossing and tooth picking is to remove debris from between and within two teeth and the associated gum. Daily plaque removal is now considered most important in that plaque and tartar build-up is considered a significant factor in causing tooth decay, gum disease, gingivitis, and periodontal disease and possibly being involved in the destruction of supporting bone structure.

Dentist routinely use metal scrapers and ultrasonic cleaners, as well, as water pressure, to remove plaque. Water picks which are available commercially require a continuous water source. Most people do not visit their dentist daily to remove plaque and film. Chemical rinses have not been sufficiently satisfactory. Direct brushing with a toothbrush immediately after eating, while effective, does not clean between teeth. It only reaches exposed surfaces. Flossing and picking between the teeth is necessary. Flossing and picking materials that will not dislodge fillings, caps, and or temporaries do not presently exist and would be very adaptive.

Tooth decay and dental disease can be caused by bacterial action resulting from the formation of plaque about the teeth and interstices there between. The removal of plaque and entrapped food particles reduces the incidence of caries, gingivitis and mouth odors. Conventional brushing is inadequate for removal of all entrapped food particles and plaques. Dental flosses, tapes are recommended.

The dental health field recommends the daily removal of plaque. Plaque can be detected by plaque detecting rinse solutions and, also, just by feeling along the surface of the teeth and interface between the gums and teeth with the tip of the tongue. The tongue feels a film and roughness that is plaque build-up, which can then be removed by flossing and picking.

Flossing and picking is thus a practical method of individual personal dental care. However, flossing and picking have disadvantages, so that less than one third of the U.S. population uses dental floss regularly.

1) Young and old do not have the dexterity, co-ordination and/or strength to manipulate floss.

2) Floss thread can dig into fingers

3) Wax coating is deposited on fingers and teeth, requiring a washing.

4) thread catches on caps, fillings, temporaries, and bridges and sometimes removes them.

5) Flossing thread cannot remove flat debris embedded in the gums, such as pop corn husks.

6) Wooden toothpicks can leave splinters.

7) Toothpicks cannot get in between the interproximal surfaces of teeth. They can only get into the triangular crevice defined by two teeth and the gum edge.

8) Toothpicks have a grain direction, which sometimes does not coincide with the direction of picking, thereby, making the toothpick easily breakable, leaving pieces of wood in between teeth.

9) Toothpicks and toothpick remainders can be left about and be eaten by children and pets. This may lead to perforation of the bowels without it being noticed. Toothpicks, after use, have an odor and are particularly attractive and dangerous to dogs and puppies.

10) Combinations of toothpick and floss such as the sword floss U.S. Pat. No. D279,826 (Shindler) has the disadvantage that if the floss is caught under a filling, the floss has to be cut from the plastic tooth pick holder. The toothpick handle on the floss in this case acts as a lever and can easily lift out a loose filling.

11) Floss and tooth picks require special dispensing and carrying devices. Floss holders are plastic containers usually resembling a compact tape dispenser and is many times larger in volume than the actual floss thread.

12) Toothpick holders are not readily available. Individually wrapped toothpicks are available; but, when carried in a pocket, it can pierce the cloth and prick the underlying skin.

Dental flossing and tooth picking, the subject matter of this invention has taken numerous forms, besides multi-filament nylon (floss) and wood (toothpicks). There are cotton threads, mono-filament, fishing line, metal wire, rubber bands as well as plastic. Forms of floss and picks are varied: plain unwaxed floss, starched floss, wax floss, strip or band floss. There are also flavored and sweetened floss, mint, cinnamon and sweet. There are wooden, plastic, metal, ivory, and bone toothpicks. They come with single, and double rounded ends. They, also, come as flat and flat at one end and rounded at the other. Tooth picks also come flavored i.e. mint. Toothpicks, however, are not usually waxed, as is floss thread, and therefore, do not have a "slipper)"aspect nor a low frictional coefficient as does waxed floss thread.

The amount of dental floss already in use in the U.S. exceeds $500 million dollars in sales (over 10 billion yards of floss is sold annually). The amount of money generated by toothpicks sales in the U.S. is comparable. Johnson and Johnson, Butler, Plackers, Strong Wood Products, and Gillette all manufacture and distribute floss and toothpicks.

OBJECT AND SUMMARY OF THE INVENTION

This invention comprises sheets of siliconized paper of sufficient width, flexibility, durability, frictional coefficient, slipperability, and foldability so as to be used as a flosser between teeth and as a paper toothpick between teeth crevices.

In addition, this invention comes as a kit containing a plurality of sheets anywhere from 1–50 sheets of the above mentioned siliconized paper in a matchbook type cover and holder.

The individual sheets and the kit can be of sufficient durability so that they can be autoclaved, heated under pressure, and/or gamma-irradiated for sterilization purposes.

In addition, the siliconized paper can be prepared with flavoring, sweeteners, dentifrices (i.e. baking soda and hydrogen peroxide) in microspheres capsules that can be affixed or embedded to the siliconized paper.

The advantage of a siliconized paperpick and floss over conventional flosses and toothpicks are:

1) It combines the advantages of each without the disadvantages in one unit. The siliconized paper can floss between teeth, like floss thread, but unlike toothpicks.

When folded with one fold the siliconized paper can scoop out large pieces between teeth. When folded with two folds resulting in a sharp, though flexible, point, it can be used as a more conventional toothpick. It has the advantage of acting with more "slipperiness" i.e. like a waxed toothpick.

2) It is easy to carry. Its volume is that of the individual sheets. Its has shape of and the convenience of a matchbook. This holder is to floss holders as matchbooks are to plastic disposable lighters.

3) Because it is siliconized, it is also waterproof. While floss is water proof, toothpicks get soggy.

4) The paper is non-toxic and if swallowed by children or pets can cause no harm.

5) It is cheaper to manufacture.

6) Flavors, sweeteners, breath deodorizers can be embedded in the siliconized paper with microspheres. This will address mouth odors and questions of taste.

7) Dentifrices such as weak solutions of baking soda and/or peroxide can be encapsulated in microspheres and embedded in the siliconized paper to allow release between teeth. This will kill bacteria and help stop gingivitis and decay.

8) Flavors, fresheners, sweeteners, and dentifrices can be empregnating in the paper by soaking, and/or stroking by brushing and/or embedding with microcapsules prior to or in conjunction with siliconization.

9) The paper pick and flosser and kit, therein, can act as an oral substitute for cigarettes and cigars. The manipulation and handling of a matchbook type holder (and something that can then be inserted into the mouth and sucked) mimics alot of the addictive behavior of cigarette and cigar smoking, without the harmful and addictive effects. Another example of using embeddable siliconized paper for oral purposes, is as a drug delivery system for oral ingestion of nicotine. This could be an alternative route to nicotine gum for assisting in quitting smoking.

DESCRIPTION OF THE PREFERRED EMBODIMENT

The new invention is designed to be a commercial product. The invention is a plurality of sheets of siliconized paper affixed in a matchbook type cover holder. The siliconized paper sheets are designed to be from 1 of 5 inches in length per side with perforations for easy ripping. They are affixed to a matchbook type cardboard cover with a hidden staple at a common border.

Figure 1:
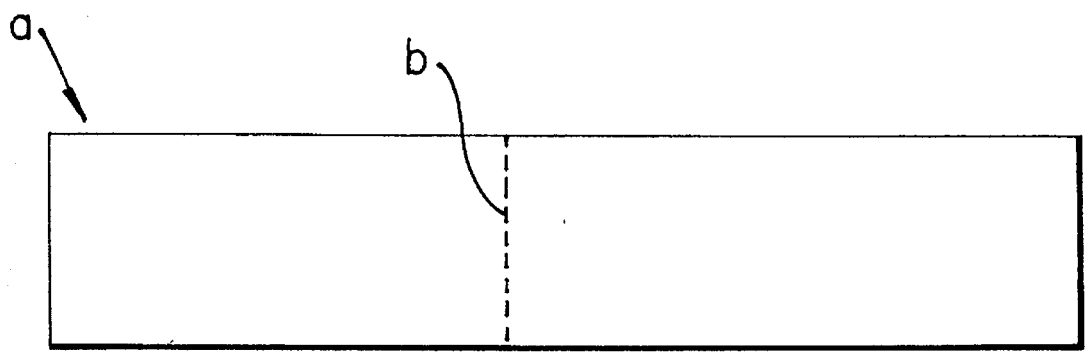
FIG. 1 is a top view of a single sheet of the flossing and picking kit of the present invention.

FIG. 1 is a top view of the element with a indicating a flossing edge. The dotted line indicated b in FIG. 1 is a foldable edge to create a scooping-type folded flossing element.

Figure 2:
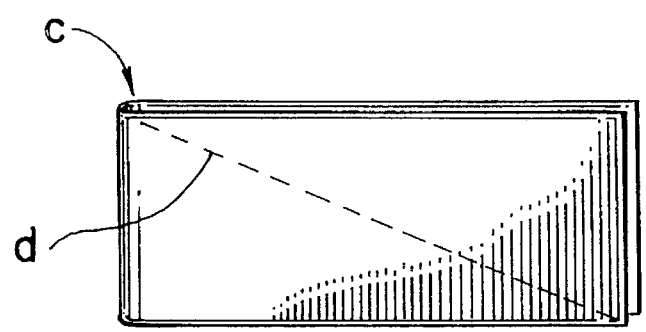
FIG. 2 is a side view of the sheet of FIG. 1 in a single fold orientation.

FIG. 2 is a side view of the element indicated in FIG. 1 singly folded creating a scoopable edge indicated as c. The dotted line indicated d is a second foldable edge to create a toothpick-like folded element.

Figure 3:
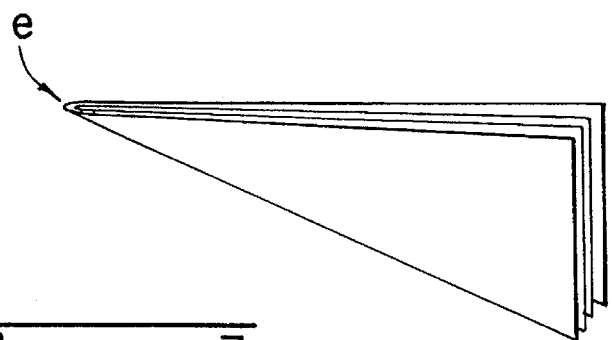
FIG. 3 is a side view of the sheet of FIG. 1 in a two-fold orientation.

FIG. 3 is a side view of the element indicated in FIG. 1 folded twice along lines b and d to create a toothpick-like folded element.

Figure 4:
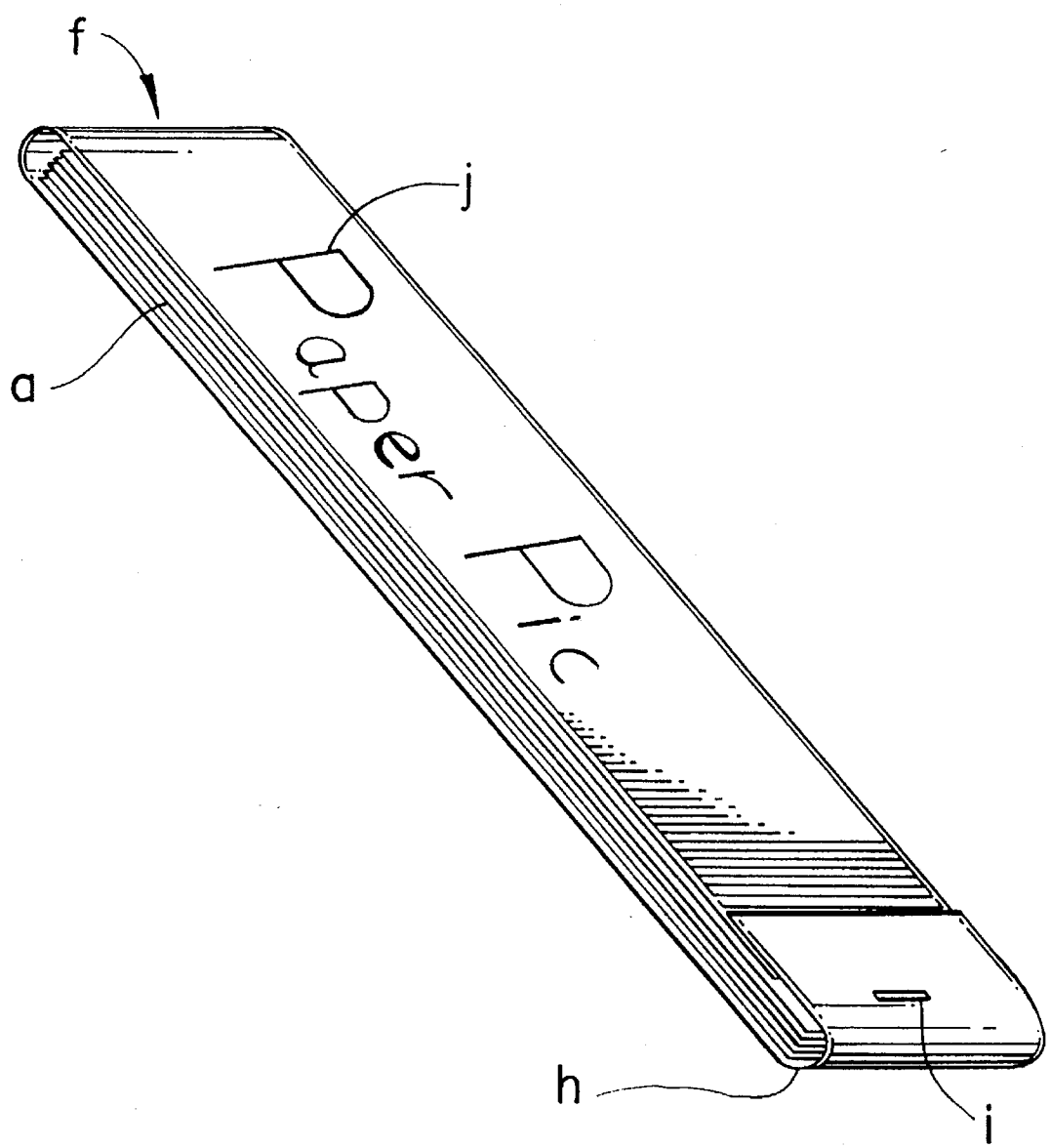
FIG. 4 is a top view of the flossing and picking kit of the present invention.

FIG. 4 is a top three-quarter view of a matchbook-like type kit containing a plurality of elements a indicating the several elements; h indicating sheets and cover cojoined at a common border; i indicating an affixing agent i.e. staple or sewn, j indicating the tradeturk name Paper Pic and advertisements, instructions, and endorsements; f indicating the flexible cover fold not affixed to the elements contained within the kit.

The siliconized paper has been tested from several type of siliconized paper of different thickness, weights, siliconization, frictional coefficient in both single and double sided forms. The preferred embodiment uses a two-faced siliconized release paper, with the following characteristics: basis weight of 53 lbs per ream, a tear strength of 53 gm/MI) or 62 gm/in CD, a tensile strength of 41 lbs/in MD or 20 lbs/in CD, a caliper of 3.2 mils, and an average release of 45 gram/2-inch strip for side 1 and 50 gram/2-inch strip for side 2.

This formulation has been tested against at least 20 other formulations of siliconized paper with a medium sized group of diverse individuals and has been found to be the most satisfactory for the following purposes.

This material shows durability for flossing, the proper thickness to insert between teeth, foldability in a point for picking in dental crevices, foldability in half for scooping and pulling out food debris between teeth. In addition siliconized paper can be formulated with microspheres containing flavoring, sweeteners, dentifrices and breath fresheners. Suitable flavors include spearmint, peppermint, wintergreen, cinnamon, cassia, menthol, Flavors such as cherry, strawberry, lime, lemon, licorice. Sweeteners such as saccharin (which has an anti-microbial effectiveness because it was originally synthesized as a sulfa drug derivative), cyclamate, aspartame, and xylitol (anti-carrie function as well as sweetener), monalin (natural or recombinant), thaumatin (natural or recombinant) can be used to temper the flavoring and breath fresheners.

Dentifrices can be mild abrasives, such as baking soda and/or dilute solutions of hydrogen peroxide (less the 0.25%). This will act as an anti-microbial and bleaching agent to both kill bacteria and whiten teeth. Dilute solutions of hydrogen peroxides are already used to sterilize paper box containers for fruit juices and milk for long term storage. The hydrogen peroxide converts to oxygen and water.

I claim:

1. A dental flossing and picking kit comprising a plurality of sheets of two-faced siliconized release paper, each of said sheets having dimensions of from 1 inch to 5 inches per side, said kit further comprising a cover which collectively envelops said sheets, said cover and said sheets being attached together along a common border.

2. The dental flossing and picking kit of claim 1, wherein each of said sheets further comprises a flavoring.

3. The dental flossing and picking kit of claim 1, wherein each of said sheets further comprises a dentifrice.

4. The dental flossing and picking kit of claim 1, wherein each of said sheets further comprises a breath freshener.

5. The dental flossing and picking kit of claim 1, wherein each of said sheets further comprises a sweetener.

* * * * *